United States Patent [19]

Aillón

[11] Patent Number: 4,601,706

[45] Date of Patent: Jul. 22, 1986

[54] CENTRAL VENOUS PRESSURE CATHETER FOR PREVENTING AIR EMBOLISM AND METHOD OF MAKING

[76] Inventor: René Aillón, 86 Crofut St., Pittsfield, Mass. 01201

[21] Appl. No.: 677,519

[22] Filed: Dec. 3, 1984

[51] Int. Cl.⁴ ............................................. A61B 5/02
[52] U.S. Cl. .................................... 604/122; 604/45;
604/53; 604/102; 128/673
[58] Field of Search ............... 604/122, 43, 45, 102,
604/126, 52-54, 280; 128/672-674

[56] References Cited

U.S. PATENT DOCUMENTS

| 4,329,993 | 5/1982 | Lieber et al. | 604/280 |
| 4,384,470 | 5/1983 | Fiore | 128/672 |
| 4,508,103 | 4/1985 | Calisi | 128/673 |

FOREIGN PATENT DOCUMENTS

| 2632280 | 1/1978 | Fed. Rep. of Germany | 604/102 |
| 2737855 | 3/1979 | Fed. Rep. of Germany | 604/102 |

OTHER PUBLICATIONS

"Transseptal Left-Heart Swan-Ganz Catheterization", *American Heart Journal*, Mar. 1983, Kotoda et al.
*British Medical Journal*, "New Appliances", Feb. 25, 1967.

Primary Examiner—Stephen C. Pellegrino
Assistant Examiner—Mark Rooney
Attorney, Agent, or Firm—Arthur K. Hooks

[57] ABSTRACT

A central venous pressure catheter has a long flexible tube containing at least three channels or lumens. At a tip end of the catheter a balloon surrounds the tube and is inflatable via one of the channels. A distal port and a proximal port in the wall of the tube are located on either side of the balloon, respectively, and are connected to the other two channels, respectively. The tip end of the catheter may be inserted via a jugular vein into a patient's superior cava vein near the heart. The balloon is inflated to partially obstruct the flow of blood and to increase the blood pressure at a site of surgery at the head or neck of a patient in the upright position to avoid air embolism as well as to prevent bleeding there. The differential pressure, e.g. in cm $H_2O$, between the two ports is made equal to the vertical distance between the distal port and the site of surgery by adjusting the size of the balloon.

3 Claims, 3 Drawing Figures

CENTRAL VENOUS PRESSURE CATHETER FOR PREVENTING AIR EMBOLISM AND METHOD OF MAKING

BACKGROUND OF THE INVENTION

This invention relates to a catheter for controllably obstructing blood flow in a vein and more particularly to such a catheter having ports on either side of the obstruction for measuring the differential pressure therebetween as a measure of the degree of obstruction obtained.

When surgery is performed on a patient in a supine (horizontal) position, air embolism is not possible because pressure within the veins is greater than atmospheric pressure. For the supine patient, open veins bleed. However, when the patient is positioned in the sitting upright position, the pressure in veins of the neck and head becomes negative in relation to atmospheric pressure, and those veins, if cut, readily draw in air.

Surgery in the upright position is a highly desirable condition sought by surgeons for certain types of operation including brain surgery, but the high probability of air inspiration into cut veins discourages and curtails this practice. Air embolism is a dreadful, insidious condition which may totally overshadow gains obtained by performing surgery in the sitting position. Air embolism can successfully be detected, but treatment, while surgery is in progress can be a nightmare. Air embolism produces a frothy blood mixture which is difficult to aspirate and attempts of air removal are often fruitless, too late and disastrous.

There is thus a long felt need for a solution to this problem.

It is therefore the object of this invention to provide a method for preventing air aspiration into cut veins and consequent air embolism during surgery of the neck and head of a patient in the sitting position.

It is a further object of this invention to provide a catheter insertable into the patient's vena cava that includes a means for controllable partial blockage of the vena cava and a means for measuring the differential blood pressure on either side of the blockage to guide blockage control.

SUMMARY OF THE INVENTION

The central venous pressure catheter of this invention is for preventing air aspiration through cut veins during surgery of the head or neck of a patient in upright position. An elongated flexible tube having multiple channels is adapted for insertion into the superior cava vein of the patient.

A pneumatically or hydraulically inflatable balloon is mounted to a portion of the multichannel tube near the distal end thereof and is connected to a first of the channels so that it's inflation may be effected by pressurizing the first channel at the other end of the tube extending outside the patient's body.

A distal port in an outer wall portion of the tube, distal from the balloon, is connected to a second of the tube channels. A proximal port in an outer wall portion of the tube on the other side of the balloon is connected to a third of the tube channels. Thus the blood pressure in the cava vein on either side of the balloon may be measured by connecting a manometer to each of the external ends of the second and third channels.

When the balloon is at least partially inflated, it presents an obstruction to the flow of blood in the cava vein and the pressure at the proximal port rises. The balloon is inflated so as to produce a differential pressure between the proximal and distal ports that raises the pressure in the veins at the site of surgery to at least zero. Without the inflated balloon obstruction, the pressure at the neck is less than zero and at the head level, less yet. When the balloon is inflated to produce a partial blockage so that the pressure at the site of surgery is zero, there is no chance of the dreaded air embolism and there is also advantageously no bleeding to obstruct the surgeons visibility.

It should be noted here that the heart serves as a pump to drive blood into the arteries, thence through a myriad of tiny capillaries all over the body and finally draw the blood from the system of paralleled capillaries via veins back to the heart. In this system the capillaries represent the load which makes up a major part of the hydraulic resistance to the flow of blood. The large arteries and veins therefore exhibit only a small blood pressure drop along their length. Thus the pressure drop from the head to the heart through veins due to blood flow alone is very small and has thus not been accunted for in the description above.

For the greatest versatility in various surgical situations the location of the ports in the central venous pressure catheter of this invention should be quite close to the balloon and thus closely spaced relative to each other, namely less than 3 cm apart. For example, it may be desirable to introduce venous catheters to a vein via a long sheath that is first inserted into the vein and attached to the skin at the point of entry. If the proximal port is located very far up the catheter from its tip, it may not yet be free of the sheath and thus render inaccurate and misleading pressure indications. However, in principle the proximal port must only be located anywhere in the blood system of the veins leading to the cava vein for proper operation. Thus the maximum spacing of the distal and proximal ports is the distance via the veins between the closest practical point of insertion, the right subclavian vein, and the right auricle of the heart, which is about 15 cm in an adult.

In summary, the manometric pressure, at a head or neck site of surgery is increased in the upright patient to zero or a positive pressure by properly inflating the balloon of the catheter of this invention. The amount of balloon inflation to provide the amount of partial blockage of blood flow in the superior cava vein that will produce a desired pressure at the site of surgery is readily determined by measuring the differential pressure between the two ports of this central venous pressure catheter.

DESCRIPTION OF THE PREFERRED EMBODIMENT

Figure 1:
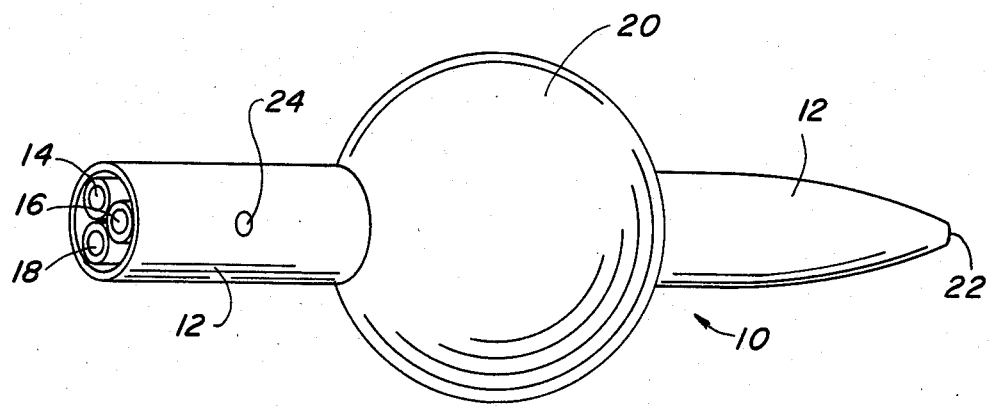
FIG. 1 shows in side view the tip end of the control venous pressure catheter of this invention.

The tip end of a multichannel central venous pressure catheter 10 of this invention illustrated in FIG. 1 includes an elongated tube or sheath 12. The tube encases three lumens 14, 16 and 18 each providing a separate pneumatic or hydraulic channel through the tube 12. An inflated balloon 20 surrounds a portion of tube 12.

Figure 2:
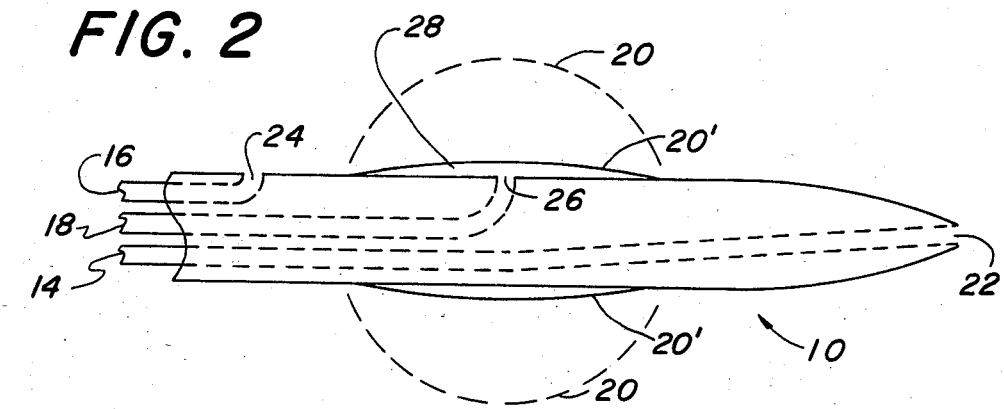
FIG. 2 shows a diagram of the tip end of the catheter of FIG. 1.

The diagram of FIG. 2 illustrates more clearly the structure of the catheter 10. Lumen 14 provides a channel through tube 12 connecting to a distal port 22 in the tube 12 at the extreme tip end thereof. Lumen 16 provides a channel through tube 12 connecting to a proximal port 24 in tube 12. Lumen 18 provides a channel connecting to a port 26 in the tube leading to the chamber 28 formed between the normally deflated elastic balloon 20' and the outer surface of the tube 12.

When lumen 18 is pressurized, the deflated balloon 20' expands and inflates as indicated by the dashed line 20. The amount of pressure in lumen 18 determines the degree of expansion of balloon 20.

The catheter 10 is designed to be inserted into the superior cava vein and for an adult human patient the tube diameter is preferably about 3 mm in diameter so as to cause minimum blockage of blood flow there. The diameter of the fully inflated balloon should be greater than 1.5 cm. Thus the volume or capacity of a fully inflated balloon of about 2 cm in length should be from 3 to 4 cc.

Figure 3:
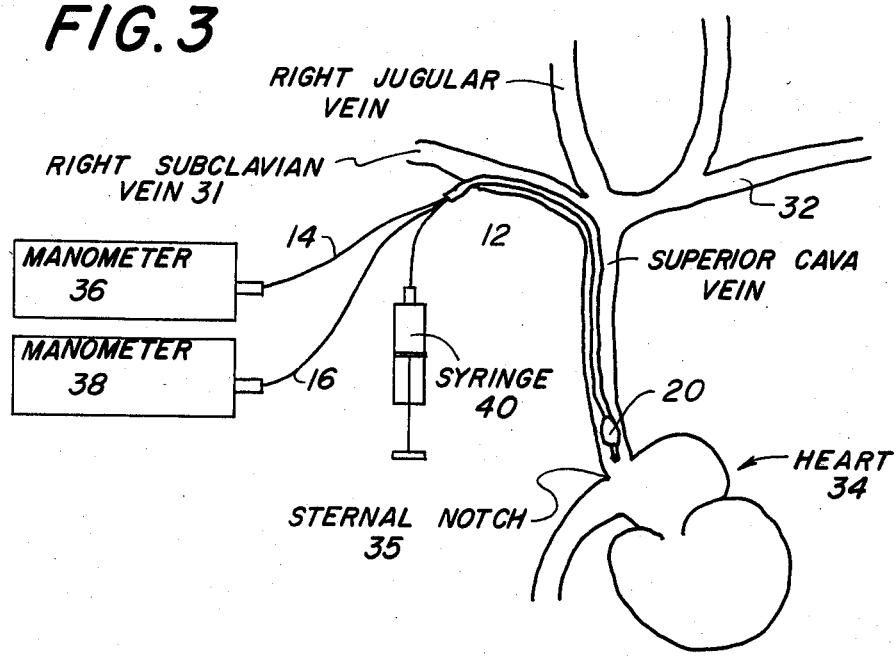
FIG. 3 shows a diagram of a portion of the cardiovascular system of a patient with the catheter of FIG. 1 properly inserted.

The catheter 10 is either inserted into the right or left jugular vein at the neck or in the right or left subclavian vein about the collar bone as is illustrated in FIG. 3.

The tip of the catheter 10 should be located near the right auricle 33 of the heart 34, i.e. not further than about 15 cm from the sternal notch 35. Accurate positioning can be accomplished by introducing into the balloon 20' via lumen 18 a saline solution mixed with an X-ray blocking dye and observing the relative catheter position by X-ray radiography.

The lumen 14 is connected to a manometer 36 and the lumen 16 is connected to another manometer 38 so that the pressures at the distal port 22 and at the proximal port 24 may be measured.

Insertion of the catheter 10 is most safely accomplished when the patient is about supine with head down, because in that position the pressure in the neck veins is positive and there is no threat of introducing air. Once insertion is accomplished, the central venous pressures at lumens 14 and 16 should be recorded, after the patient's position is returned to horizontal.

These pressures about 8 cm $H_2$), should be equal to each other. The patient then is asked to sit up. New pressure readings should be recorded. The differential pressure will correspond (in centimeters of water, or cm $H_2O$) to the distance (in centimeters between the distal port 22 and the proximal port 24) the pressure at proximal port 24 being the lesser. The deflated balloon 20' is then slowly inflated by squeezing the syringe 40 that is filled with a saline solution. The pressure at the proximal port 24 will increase. When the pressure difference between ports 22 and 24 equals, in cm $H_2O$, the vertical distance between the distal port 22 and the site at the head or neck at which surgery is to begin, then the balloon 20 is optimally expanded to create a pressure at the site of surgery such that neither bleeding nor air embolism will occur. The balloon is deflated, the patient is returned to horizontal position. Anesthesia begins. The patient then is positioned (sit up) to the desired level for proper surgical exposure. New pressure readings are made, before surgery begins. The balloon 20' is slowly inflated in increments of 0.5 cc until the differential pressure readings in monometers 36 and 38 indicate "zero" pressure at the middle of the surgical insicion.

Changes in cardiac output, will cause a change in the differential pressure between catheter ports 22 and 24, and it is therefore necessary to continously monitor the differential pressure and make readjustments of the balloon pressure and size to maintain the above-noted optimum pressure differential. Adequate anesthesia levels can usually be administered to substantially stabilize cardiac output. However, it is anticipated that automatic means may be employed, if necessary to sense the differential ports pressure and make the indicated balloon size adjustments.

What is claimed is:

1. A method for preventing air embolism in a patient in an upright position undergoing surgery of the head or neck comprising:
   (a) inserting a central-venous-pressure multichannel catheter via a subclavian or a jugular vein just into the patient's superior cava vein so that an inflatable balloon portion of said catheter is located in said cava vein near the left artrium of the heart, a distal port and a proximal port of said catheter being spaced apart and on either side, respectively of said balloon;
   (b) measuring the differential pressure between said proximal and distal ports; and
   (c) inflating said balloon to partially obstruct the blood flow in said cava vein and raise said measured differential pressure to the blood manometric pressure level corresponding to the vertical distance between said distal port and the site of said surgery so that the blood pressure at the site of surgery relative to the environment is near zero.

2. The method of claim 1 wherein said distal and proximal ports are spaced no farther apart than 15 centimeters.

3. The method of claim 2 wherein said distal and proximal ports are spaced no further apart than 3 centimeters.

* * * * *